United States Patent [19]
Robinson

[11] Patent Number: 5,840,069
[45] Date of Patent: Nov. 24, 1998

[54] IMPLANTABLE PERISTALTIC PUMP TECHNIQUES

[75] Inventor: Reginald D. Robinson, Brooklyn Park, Minn.

[73] Assignee: Medtronic, Inc., Minneapolis, Minn.

[21] Appl. No.: 627,985

[22] Filed: Apr. 4, 1996

[51] Int. Cl.$^6$ ............ A61M 37/00; A61M 1/00; F04B 43/09; F04B 43/12
[52] U.S. Cl. ............ 604/131; 604/153; 417/477.3
[58] Field of Search ............ 604/131–133, 604/151, 153; 417/476, 477.1, 477.3, 477.5, 477.6

[56] References Cited

U.S. PATENT DOCUMENTS

| | | | |
|---|---|---|---|
| 2,920,578 | 1/1960 | Schaurte | 417/477 |
| 3,918,453 | 11/1975 | Leonard | 604/153 X |
| 3,990,444 | 11/1976 | Vial | 604/153 X |
| 4,012,177 | 3/1977 | Yakich | 604/153 X |
| 4,256,437 | 3/1981 | Brown | 604/153 X |
| 4,525,164 | 6/1985 | Loeb et al. | 604/131 |
| 4,576,556 | 3/1986 | Thompson . | |
| 4,650,471 | 3/1987 | Tamari | 604/153 |
| 4,685,902 | 8/1987 | Edwards et al. | 604/153 |
| 4,692,147 | 9/1987 | Duggan . | |
| 4,950,136 | 8/1990 | Haas et al. | 604/153 X |
| 5,064,358 | 11/1991 | Calari | 604/153 X |
| 5,082,429 | 1/1992 | Soderquist et al. | 604/153 X |
| 5,083,908 | 1/1992 | Gagnebin et al. | 604/153 X |
| 5,096,393 | 3/1992 | Van Steenderen et al. | 604/153 X |
| 5,213,483 | 5/1993 | Flaherty et al. | 604/153 X |
| 5,266,013 | 11/1993 | Aubert et al. | 604/153 X |
| 5,578,001 | 11/1996 | Shah | 604/132 X |

FOREIGN PATENT DOCUMENTS

| | | | |
|---|---|---|---|
| 3737023 | 7/1988 | Germany | 417/477.5 |
| 547550 | 5/1977 | U.S.S.R. | 417/476 |
| 681 | of 1902 | United Kingdom | 417/477.3 |

*Primary Examiner*—Danton D. DeMille
*Attorney, Agent, or Firm*—Banner & Witcoff Ltd

[57] ABSTRACT

A peristaltic pump for an implantable medical device includes a pump tube defining an axis lying along a path in a first plane. Spherical rollers compress the tube at one or more points along the path in a direction non-parallel to the first plane, and preferably perpendicular to the first plane. Means for driving the rollers are provided so that liquid is moved through the tube.

28 Claims, 2 Drawing Sheets

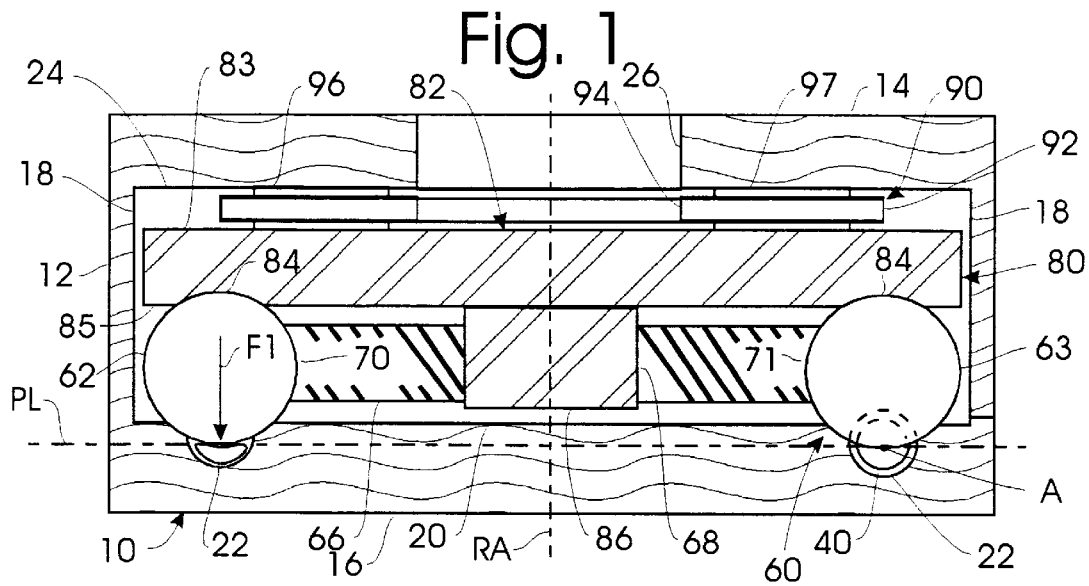
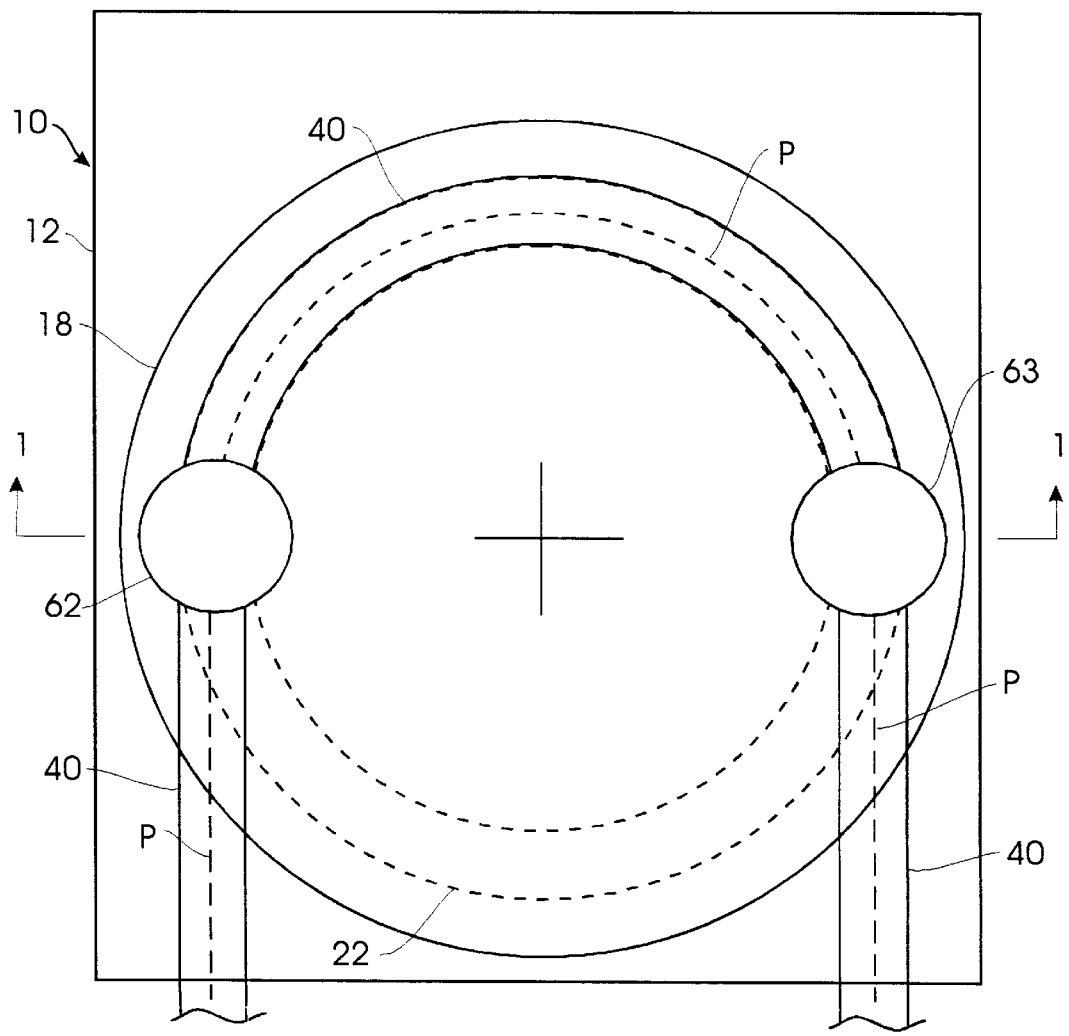

IMPLANTABLE PERISTALTIC PUMP TECHNIQUES

BACKGROUND OF THE INVENTION

1. Field of the Invention

This invention relates to implantable pumps for infusing a therapeutic agent into an organism, and more particularly relates to such a pump for simulating peristaltic motion.

2. Description of the Related Art

Peristaltic pumps have been designed in the past, and one example is shown in U.S. Pat. No. 4,692,147 (Duggan) ("the '147 Patent"), assigned to Medtronic, Inc., Minneapolis, Minn. Although the pump described by Duggan provides highly accurate peristaltic pump operation, experience has shown that it requires close tolerances and accurate machining of some pump components which adds considerably to manufacturing expense. The pump tube described by Duggan is extruded with flanges or wings protruding from the outer wall of the tube. These features help insure that the pump tube remains aligned in a race. However, the presence of the flange increases costs by complicating the tube fabrication process. The pump race requires additional depth to accommodate the wings and adds to the inherent thickness of the pump assembly. The pump described by Duggan requires careful alignment of the pump tube, a shim and a roller that cause occlusion of the tube. The alignment procedure has proven to be time consuming and expensive. The present invention eliminates the expense and assembly difficulties associated with the peristaltic pump described by Duggan while maintaining the accuracy of the drug dosage delivered by the pump.

SUMMARY OF THE INVENTION

A peristaltic pump made in accordance with the invention is suitable for an implantable medical device. According to a preferred embodiment, a pump tube holds liquid to be pumped, and the tube defines an axis lying along a path. A first race supports the tube in a first plane. Roller means compress the tube at one or more points along the path in a direction non-parallel to the first plane. Means are provided for moving the roller means relative to the tube along the path so that liquid is moved through the tube. By using the foregoing arrangement, a highly accurate peristaltic pump can be fabricated with low tolerances. No machining is required, and the pump parts are easily assembled.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 1 is a cross-sectional view of a preferred form of pump made in accordance with the present invention taken along line 1—1 in FIG. 2;

FIG. 2 is a top plan view of the pump shown in FIG. 1 with the top portion of the housing and the roller assembly removed to reveal the inner parts.

DESCRIPTION OF THE PREFERRED EMBODIMENTS

Figure 3:
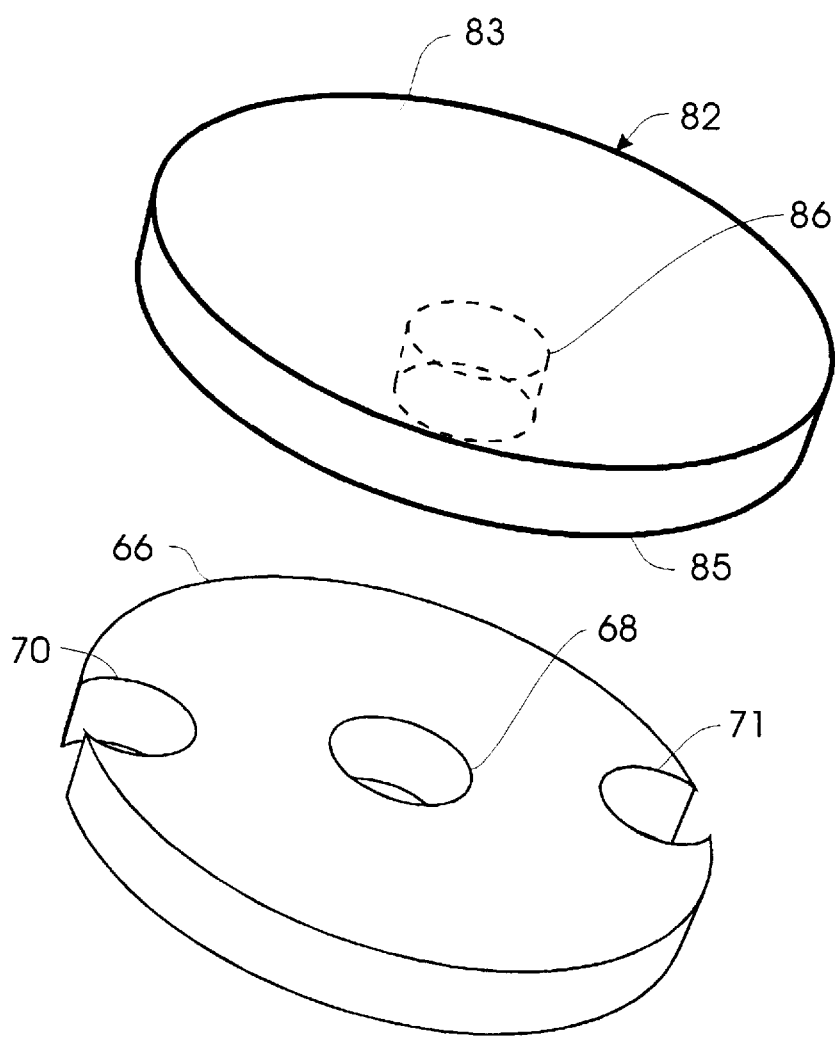
FIG. 3 is a perspective view of two of the parts shown in FIG. 1.

Referring to FIG. 1, a preferred form of peristaltic pump made in accordance with the present invention basically comprises a housing 10, a peristaltic pump tube 40, a roller assembly 60, a drive assembly 80, and a bearing assembly 90.

Referring to FIGS. 1 and 2, housing 10 comprises an outer surface 12, a top surface 14 and a bottom surface 16. Housing 10 defines a cylindrical inner wall 18, as well as an inner bottom surface 20 that defines a circular race or depression 22. Housing 10 also includes an inner top surface 24 defining a central cylindrical opening 26 to allow the entry of a drive mechanism to turn the pump. The housing can be broken into top and bottom segments (not shown) for ease of assembly.

Peristaltic pump tube 40 is a flexible tube having an inner diameter of 0.040 inch, an outer diameter of 0.060 inch and preferably is fabricated from silicone rubber. Tube 40 has a cylindrical cross-section that defines an axis A and extends through a path P. As shown in FIG. 1, axis A lies in a plane PL. Tube 40 is supported by surface 20 in depression 22.

Roller assembly 60 comprises rollers 62 and 63 that are conventional, spherical ball-bearings. Assembly 60 also includes a spacer 66 fabricated from PTFE. Spacer 60 defines a central opening 68 and includes cylindrical cut out portions 70 and 71 that contain and guide rollers 62 and 63 (FIG. 3).

Drive assembly 80 includes a disk 82 having a top surface 83 and a bottom surface 85 that forms a circular roller race 84 adapted to comate with rollers 62 and 63. Integrally formed with disk 82 is a depending collar 86 that fits into and rotates within opening 68 of spacer 66 (FIGS. 1 and 3). Disk 82 rotates around an axis RA in order to drive rollers 62 and 63 around axis RA.

As shown in FIG. 1, rollers 62 and 63 exert an occlusion force, such as F1, perpendicular to plane PL in order to compress tube 40 in the manner shown in the left-hand portion of FIG. 1. Tube 40 is shown in phantom in the right-hand portion of FIG. 1 in its uncompressed state for purposes of comparison with the compressed state. However, roller 63 in fact compresses tube 40 as shown under arrow F1. Having force F1 applied to tube 40 in a non-parallel direction relative to plane PL offers a distinct advantage which allows for ease of assembly and requires no machining or close tolerances of parts.

Bearing assembly 90 comprises a conventional roller bearing 92 defining a central opening 94 and including a plurality of rollers, such as 96 and 97. A drive mechanism from a pump motor may be attached to the top surface of disk 82 through openings 26 and 94 (FIG. 1). The pump may be driven by the same motor described in the '147 Patent.

Spacer 66 may accommodate two or more rollers depending on the type of motor used to drive the pump and the rate of liquid flow required from tube 40. Rather than using roller bearing 92, the top inner surface 24 of the housing and the top surface 83 of disk 82 can be made from low-friction material, like PTFE, thereby eliminating the necessity for a roller bearing or ball-bearing assembly.

In order to assemble the pump, tube 40 is bonded in the pump tube groove 22, and rollers 62 and 63 are placed in cut out portions 70 and 71 of spacer 66. Drive disk 82 is placed on top of the roller assembly and is coupled with a motor. As disk 82 turns around axis RA, the spacer 66 and rollers 62 and 63 rotate around axis RA approximately 0.5° for every 1.0° of disk 82 rotation. Fluid from a pressurized reservoir is pushed along inside tube 40 ahead of the advancing rollers in the manner of a conventional peristaltic pump. As rollers 62 and 63 advance along path P, they compress tube 40 as shown in the left-hand portion of FIG. 1, thereby moving liquid through the tube in the direction of travel of the rollers. Rollers 62 and 63 are advanced solely by friction from disk 82. This is an important feature which contributes to the ability of the pump to provide the precise operation without the necessity for machine parts or holding close tolerances.

Those skilled in the art recognize that the preferred embodiments may be altered and modified without departing from the true spirit and scope of the invention as defined in the appended claims. For example, the occlusion force F1 could be generated by springs, bellows and propellant, bellows and direct or amplified reservoir pressure, or other means of exerting force on the rollers.

I claim:

1. A peristaltic pump for an implantable medical device comprising in combination:

a pump tube for holding a liquid to be pumped, said tube defining an axis lying along a path;

a first race for supporting said tube in a first plane;

roller means for compressing said tube at one or more points along said path in a direction non-parallel to said first plane, said roller means comprising at least one spherical roller and a spacer for guiding said at least one roller along said path; and means for driving said roller means relative to said tube along said path, whereby said liquid is moved through said tube.

2. A pump, as claimed in claim 1, wherein said means for driving comprises a second race for urging said roller against said tube.

3. A pump, as claimed in claim 2, wherein said second race is rotatable against said one or more rollers, whereby said one or more rollers are driven along said path.

4. A pump, as claimed in claim 3, wherein said one or more rollers are moved along said path by friction with said second race.

5. A pump, as claimed in claim 3, wherein said spacer defines a central opening and wherein said second race comprises a member that comates with said opening, whereby said spacer is held in a position enabling said one or more rollers to move along said path.

6. A pump, as claimed in claim 5, and further comprising a housing for said pump, said housing comprising a side wall for confining said first race, roller means and means for driving in an operative relationship with respect to said tube.

7. A pump, as claimed in claim 6, wherein said second race moves relative to said housing on a bearing.

8. A pump, as claimed in claim 7, wherein said bearing comprises a roller bearing.

9. A pump, as claimed in claim 1, wherein said roller means comprises two or more spherical rollers.

10. A peristaltic pump for implantable medical devices comprising in combination:

a pump tube for holding a liquid to be pumped;

a first race for supporting said tube in a circular path defining a first plane;

roller means for compressing said tube at one or more points along said path in a direction non-parallel to said first plane; wherein said roller means comprises at least one spherical roller and a spacer for guiding said at least one roller along said path and means for driving said roller means relative to said tube along said path, whereby liquid is moved through said tube.

11. A pump, as claimed in claim 10, wherein said tube is cylindrical, wherein said path defines a circle and wherein said axis defines a circle.

12. A pump, as claimed in claim 10, wherein said first race comprises a circular depression for holding said tube.

13. A pump, as claimed in claim 10, wherein said means for driving comprises a second race for urging said roller against said tube.

14. A pump, as claimed in claim 13, wherein said second race is rotatable against said one or more rollers, whereby said one or more rollers are driven along said path.

15. A pump, as claimed in claim 14, wherein said one or more rollers are moved along said path by friction with said second race.

16. A pump, as claimed in claim 14, wherein said spacer defines a central opening and wherein said second race comprises a member that comates with said opening, whereby said spacer is held in a position enabling said one or more rollers to move along said path.

17. A pump, as claimed in claim 16, and further comprising a housing for said pump, said housing comprising a side wall for confining said first race, roller means and means for driving in an operative relationship with respect to said tube.

18. A pump, as claimed in claim 17, wherein said second race moves relative to said housing on a bearing.

19. A pump, as claimed in claim 18, wherein said bearing comprises a roller bearing.

20. A pump, as claimed in claim 10, wherein said direction is perpendicular to said plane.

21. A pump, as claimed in claim 10, wherein said roller means comprises two or more spherical rollers.

22. A peristaltic pump comprising:

a pump tube for holding a liquid to be pumped, the pump tube extending in an arcuate path to define a first plane;

a race for supporting the pump tube;

a roller for compressing the pump tube to advance the liquid; and a drive assembly for driving the roller along the arcuate path, the drive assembly cooperating with the roller such that the roller applies an occluding force to the tube in a direction non-parallel to the first plane wherein the drive assembly comprises a disk having a surface that engages the roller and a spacer for guiding the roller for movement along the arcuate path and wherein the spacer includes an opening and the disk comprises a collar adapted to fit within the opening.

23. The pump according to claim 22, whrein the roller is spherical.

24. The pump according to claim 22, wherein the disk is adapted to rotate in a second plane that is parallel to the first plane.

25. The pump according to claim 24, wherein the roller is adapted to advance in a plane parallel to the first and second planes.

26. The pump according to claim 22, wherein the occluding force is transmitted from the drive assembly through the roller in a direction non-parallel to the first plane.

27. The pump according to claim 22, wherein the drive assembly rotates about a drive assembly rotational axis and wherein the roller rotates about a roller rotational axis non-parallel to the drive assembly rotational axis.

28. The pump according to claim 27, wherein the drive assembly rotational axis is perpendicular to the roller rotational axis.

* * * * *